United States Patent [19]

Priesnitz et al.

[11] Patent Number: 4,659,822
[45] Date of Patent: Apr. 21, 1987

[54] PROCESS FOR THE PREPARATION OF 2-CYANOAMINO-1,3,5-TRIAZINES

[75] Inventors: Uwe Priesnitz, Solingen; Hans-Jochem Riebel, Wuppertal, both of Fed. Rep. of Germany

[73] Assignee: Bayer Aktiengesellschaft, Leverkusen, Fed. Rep. of Germany

[21] Appl. No.: 829,670

[22] Filed: Feb. 13, 1986

[30] Foreign Application Priority Data

Mar. 5, 1985 [DE] Fed. Rep. of Germany ....... 3507751

[51] Int. Cl.⁴ ................... C07D 251/16; C07D 251/18
[52] U.S. Cl. ..................................... 544/194; 544/204
[58] Field of Search ............................... 544/194, 204

[56] References Cited

U.S. PATENT DOCUMENTS 3,053,843  9/1962  Gysin et al. ......................... 544/194
3,152,127 10/1964  Sallmann et al. ................ 544/204 X
3,419,556 12/1968  Schubert et al. ................ 544/204 X

FOREIGN PATENT DOCUMENTS 0121082 10/1984  European Pat. Off. .
3334455  9/1984  Fed. Rep. of Germany .

OTHER PUBLICATIONS

Fieser et al, Reagents for Organic Synthesis, vol. 8, (1980), p. 191, Wiley Interscience, N.Y.
J. Heterocyclic Chem., vol. 19, pp. 577–583, (1982), Stanovnik et al.

*Primary Examiner*—Joseph Paul Brust
*Attorney, Agent, or Firm*—Sprung Horn Kramer & Woods

[57] ABSTRACT

The novel process

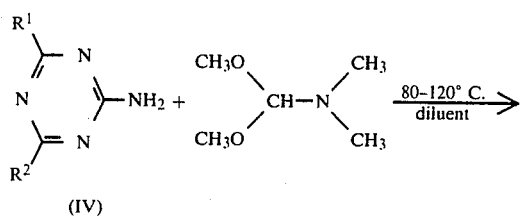

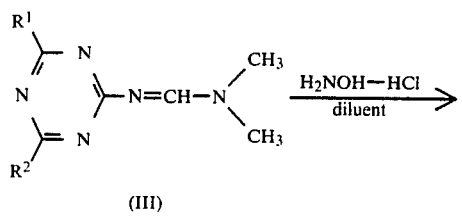

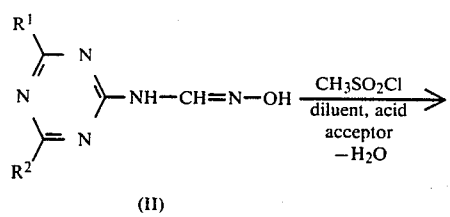

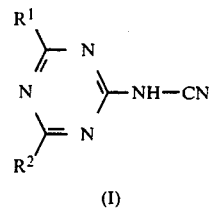

in which
  $R^1$ is alkyl, and
  $R^2$ is alkoxy, alkylamino or dialkylamino.

Compounds II and III are new, while (I) is a known intermediate for herbicides.

3 Claims, No Drawings

PROCESS FOR THE PREPARATION OF 2-CYANOAMINO-1,3,5-TRIAZINES

The present invention relates to a new process for the preparation of 2-cyanoamino-1,3,5-triazines, and new intermediate products for this process. The process products are known in some cases, and they can be used as intermediate products for the preparation of herbicides and plant growth regulators.

It is already known that 2-cyanoamino-1,3,5-triazines are obtained by reacting alkali metal or alkaline earth metal salts of cyanamide with the corresponding 2-halogeno-1,3,5-triazines. See Ser. No. 578,345 filed Feb. 9, 1984, now pending.

However, this process has only a limited applicability because of the unsatisfactory methods for the preparation of the 2-halogeno-1,3,5-triazines.

It has now been found that 2-cyanoamino-1,3,5-triazines of the general formula (I)

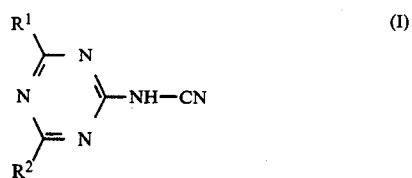

in which
  $R^1$ represents alkyl and
  $R^2$ represents alkoxy, alkylamino or dialkylamino, are obtained by a process in which oximes of the formula (II)

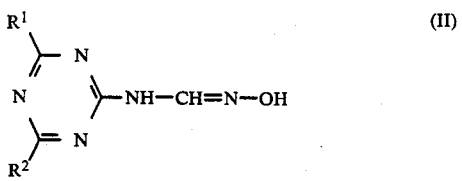

in which
  $R^1$ and $R^2$ have the abovementioned meanings, are reacted with methanesulphonyl chloride in the presence of acid acceptors and in the presence of diluents.

Surprisingly, it is possible to carry out dehydration of the oximes with the aid of the process according to the invention. According to the prior art, dehydration of chemically similar compounds with, for example, phosphorus oxychloride is not possible or gives only very poor yields (J. Het. Chem. 19, 577 (1982)).

Compounds of the formula (I) which are preferably prepared with the aid of the process according to the invention are those in which
  $R^1$ represents alkyl with 1 to 6 carbon atoms and
  $R^2$ represents alkoxy with 1 to 6 carbon atoms or alkylamino or dialkylamino with in each case 1 to 6 carbon atoms in the alkyl part.

Compounds of the formula (I) which are particularly preferably prepared are those in which
  $R^1$ represents $C_1$–$C_4$-alkyl and
  $R^2$ represents $C_1$–$C_4$-alkoxy, $C_1$–$C_4$-alkylamino or di-($C_1$–$C_4$)-alkylamino.

Compounds of the formula (I) which are especially preferably prepared are those in which
  $R^1$ represents methyl, ethyl, n-propyl, i-propyl or n-butyl and
  $R^2$ represents methoxy, ethoxy, n-propoxy, i-propoxy, n-butoxy, (di)methylamino, (di)ethylamino, (di)n-propylamino, (di)i-propylamino, (di)n-butylamino, (di)i-butylamino, (di)sec.-butylamino, tert.-butylamino, ethylmethylamino, methyl-n-propylamino, methyl-i-propylamino, methyl-n-butylamino, methyl-i-butylamino, ethyl-n-propylamino, ethyl-i-propylamino, ethyl-n-butylamino, ethyl-i-butylamino, n-propyl-i-propylamino, n-propyl-n-butylamino, n-propyl-i-butylamino, i-propyl-n-butylamino, i-propyl-i-butylamino or n-butyl-i-butylamino.

If, for example, N-(4-ethoxy-6-methyl-1,3,5-triazin-2-yl)-formamide oxime and methanesulphonyl chloride are used as starting substances for the process according to the invention, the reaction can be represented by the following equation:

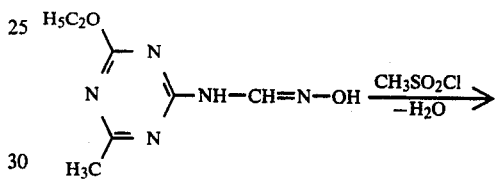

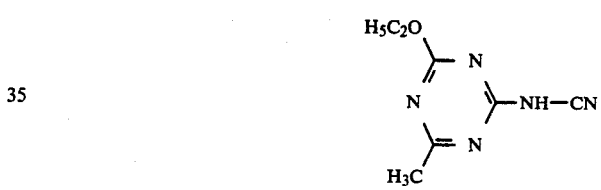

Formula (II) provides a general definition of the oximes to be used as starting substances for the process according to the invention. In this formula, preferably,
  $R^1$ represents alkyl with 1 to 6 carbon atoms and
  $R^2$ represents alkoxy with 1 to 6 carbon atoms or alkylamino or dialkylamino with in each case 1 to 6 carbon atoms in the alkyl part.

Particularly preferred compounds of the formula (II) are those in which
  $R^1$ represents $C_1$–$C_4$-alkyl and
  $R^2$ represents $C_1$–$C_4$-alkoxy, $C_1$–$C_4$-alkylamino or di-($C_1$–$C_4$)-alkylamino.

Especially preferred compounds of the formula (II) are those in which
  $R^1$ represents methyl, ethyl, n-propyl, i-propyl or n-butyl and
  $R^2$ represents methoxy, ethoxy, n-propoxy, i-propoxy, n-butoxy, (di)methylamino, (di)ethylamino, (di)n-propylamino, (di)i-propylamino, (di)n-butylamino, (di)i-butylamino, (di)sec.-butylamino or tert.-butylamino.

The compounds of the formula (II) are new. They can be prepared by known methods, for example as follows, by a process in which formamidines of the formula (III)

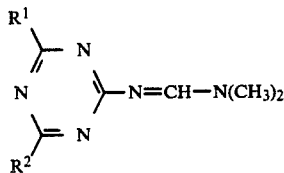

in which R¹ and R² have the abovementioned meanings, are reacted with hydroxylamine hydrochloride in the presence of a diluent, such as, for example, methanol or dimethylformamide, at temperatures between 15° C. and 30° C.

The formamidines of the formula (III) are likewise new. They can be prepared by known methods, for example by reacting 2-amino-1,3,5-triazines of the formula (IV)

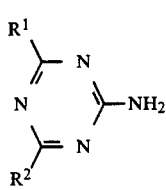

in which R¹ and R² have the abovementioned meanings, with dimethylformamide dimethyl acetal in the presence of a diluent, such as, for example, toluene, at temperatures between 80° C. and 120° C.

The compounds of the formula (IV) are known compounds of organic chemistry.

Formula (III) provides a general definition of the formamidines which are employed as starting substances for the preparation of the compounds of the formula (II). In this formula (III), R¹ and R² preferably and particularly preferably represent those radicals which have been mentioned as preferred or as particularly preferred for these substituents in formula (II).

The process according to the invention for the preparation of the compounds of the formula (I) is carried out in the presence of inert diluents.

These include, in particular, aliphatic hydrocarbons, such as hexane, and furthermore ethers, such as diethyl ether, dibutyl ether, glycol dimethyl ether, diglycol dimethyl ether, tetrahydrofuran and dioxane, amides, such as, for example, dimethylformamide, dimethylacetamide and N-methylpyrrolidone, and dimethylsulphoxide, tetramethylene sulphone and hexamethylphosphoric acid triamide.

The process according to the invention is carried out in the presence of acid acceptors. Acid acceptors which can be used are all the customary acid-binding agents. Acid-binding agents which have proved particularly suitable are alkali metal carbonates, such as sodium carbonate and potassium carbonate, and furthermore aliphatic, aromatic or heterocyclic amines, for example triethylamine, trimethylamine, dimethylaniline, dimethylbenzylamine and pyridine.

The process according to the invention is in general carried out at temperatures between 0° C. and +160° C. The range between 20° C. and 140° C. is preferred. The reactions are in general carried out under normal pressure.

The starting substances are usually employed in equimolar amounts for carrying out the process according to the invention. An excess of one or other of the reaction components provides no substantial advantages. The reaction is carried out in a suitable diluent in the presence of an acid acceptor, and the reaction mixture is stirred at the required temperature. Thereafter, an organic solvent, for example methylene chloride, is added and the organic phase is worked up in the customary manner by washing, drying and distilling off the solvent.

The 2-cyanoamino-1,3,5-triazines to be prepared by the process according to the invention can be employed as intermediate products for the preparation of guanidine derivatives, which are active as herbicides and plant growth regulators (compare EP-OS (European Published Specification) No. 121,082).

PREPARATION EXAMPLES

Example 1

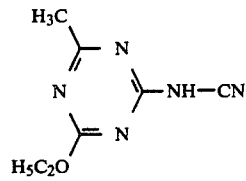

12.5 g (0.11 mole) of methanesulphonyl chloride are added to a mixture of 20 g (0.1 mole) of N-(4-ethoxy-6-methyl-1,3,5-triazin-2-yl)-formamide oxime in 400 ml of glycol dimethyl ether and the mixture is heated under reflux for 2 hours. After cooling to 20° C., a mixture of 8 g of triethylamine and 20 ml of glycol dimethyl ether is added and the mixture is heated under reflux for 1 hour. The hydrochloric acid is then neutralized, the mixture is evaporated to dryness and the residue is taken up in 100 ml of methylene chloride.

The concentration of 2-cyanoamino-4-ethoxy-6-methyl-1,3,5-triazine is determined analytically by means of the "external standard method". Based on this concentration, the yield is 50% of theory.

The target compound can be prepared in a highly pure form after purification by chromatography and is characterized by its ¹H-NMR spectrum.

¹H-NMR (CDCl₃) δ=1.38 (t, CH₃—CH₂); 2.36 (S, CH₃); 4.38 (q, CH₂—CH₃); H$_{\frac{1}{2}}$=5 Hz; and 6.17 (br, —NH) ppm.

Melting point: 195° C. (decomposition).

The following compound of the formula (I) can be obtained analogously to Example 1:

Example 2

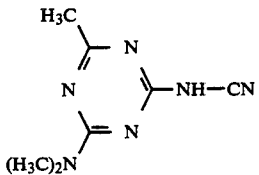

Starting compounds of the formula (II)

Example (II-1)

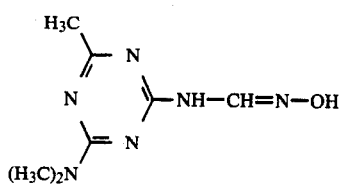

21 g (0.3 mole) of hydroxylamine hydrochloride are added to a solution of 52 g (0.25 mole) of N,N-dimethyl-N'-(4-dimethylamino-6-methyl-1,3,5-triazin-2-yl)-formamidine in 400 ml of methanol and the mixture is subsequently stirred at 20° C. for 3 hours.

After filtration, 49 g (100% of theory) of N-(4-dimethylamino-6-methyl-1,3,5-triazin-2-yl)-formamide oxime of melting point 256° C. are obtained.

The following compound of the formula (II) can be prepared analogously to Example (II-1):

Example (II-2)

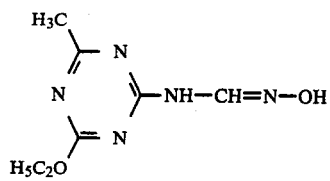

Melting point: 233° C.

Example (II-3)

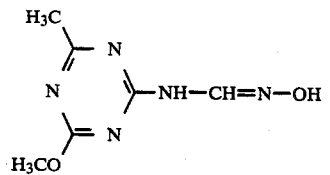

Melting point >220° C.

Starting compounds of the formula (III)

Example (III-1)

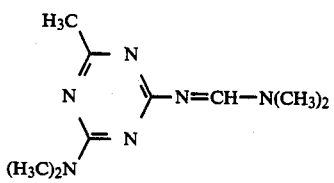

A mixture of 50 g (0.327 mole) of 2-amino-4-dimethylamino-6-methyl-1,3,5-triazine, 55 ml (0.59 mole) of dimethylformamide dimethyl acetal and 300 ml of toluene is heated under reflux for 5 hours and then concentrated.

67 g (100% of theory) of N,N-dimethyl-N'-(4-dimethylamino-6-methyl-1,3,5-triazin-2-yl)-formamidine of melting point 61° C. are obtained.

The following compound of the formula (III) can be obtained analogously to Example (III-1):

Example (III-2)

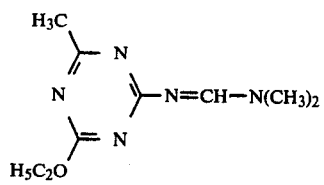

Melting point: 48° C.

Example (III-3)

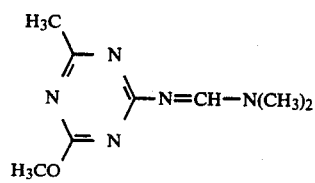

Melting point: 58° C.

It is understood that the specification and examples are illustrative but not limitative of the present invention and that other embodiments within the spirit and scope of the invention will suggest themselves to those skilled in the art.

What is claimed is:

1. A process for the preparation of a 2-cyanoamino-1,3,5-triazine of the formula

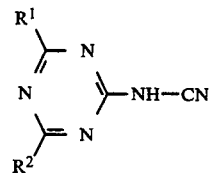

in which
$R^1$ is alkyl with 1 to 6 carbon atoms, and
$R^2$ is alkoxy, alkylamino or dialkylamino with 1 to 6 carbon atoms in each alkyl radical,
which comprises reacting an oxime of the formula

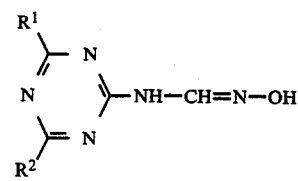

with methanesulphonyl chloride in the presence of an acid acceptor and in the presence of a diluent at a temperature between about 0° and 160° C.

2. An oxime of the formula

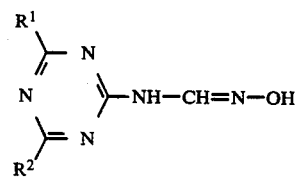

in which
R¹ is alkyl with 1 to 6 carbon atoms, and
R² is alkoxy, alkylamino or dialkylamino with 1 to 6 carbon atoms in each alkyl radical.
3. A formamidine of the formula
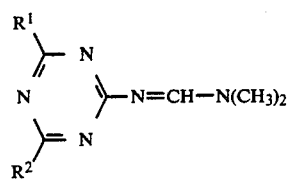
in which
R¹ is alkyl, with 1 to 6 carbon atoms, and
R² is alkoxy, alkylamino or dialkylamino with 1 to 6 carbon atoms in each alkyl radical.
* * * * *